United States Patent [19]
Lesieur et al.

[11] Patent Number: 5,668,180
[45] Date of Patent: Sep. 16, 1997

[54] ALKOXYARYL COMPOUNDS

[75] Inventors: Daniel Lesieur, Gondecourt; Patrick Depreux, Armentieres; Véronique Leclerc, Lille; Philippe Delagrange, Issy les Moulineaux; Pierre Renard, Versailles, all of France

[73] Assignee: Adir Et Compagnie, Courbevoie, France

[21] Appl. No.: 655,439

[22] Filed: May 30, 1996

[30] Foreign Application Priority Data

May 31, 1995 [FR] France ............... 95 06434

[51] Int. Cl.$^6$ ............... A61K 31/16; C07C 233/05
[52] U.S. Cl. ............... 514/630; 514/585; 514/586; 514/595; 514/599; 514/629; 514/415; 514/443; 514/469; 514/929; 548/491; 548/504; 548/507; 549/51; 549/407; 564/26; 564/28; 564/56; 564/74; 564/215; 564/217; 564/218; 564/219
[58] Field of Search ............... 564/74, 215, 217, 564/218, 219, 56, 26, 28; 514/599, 595, 585, 586, 629, 630, 415, 443, 469, 929; 548/491, 504, 507; 549/51, 407

[56] References Cited

U.S. PATENT DOCUMENTS

| | | | |
|---|---|---|---|
| 5,071,875 | 12/1991 | Horn et al. | 514/613 |
| 5,194,614 | 3/1993 | Andrieux et al. | 544/400 |
| 5,385,944 | 1/1995 | Lesieur et al. | 514/585 |
| 5,449,689 | 9/1995 | Lesieur et al. | 514/585 |
| 5,449,690 | 9/1995 | Lesieur et al. | 514/596 |
| 5,571,810 | 11/1996 | Matsuo et al. | 514/231.5 |
| 5,591,775 | 1/1997 | Depreux et al. | 514/580 |
| 5,604,261 | 2/1997 | Langlois et al. | 514/630 |

*Primary Examiner*—Shailendra Kumar
*Attorney, Agent, or Firm*—The Firm of Gordon W. Hueschen

[57] ABSTRACT

A compound selected from those of formula (I):

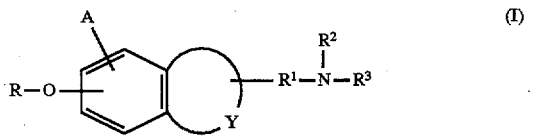

in which A, R, Y, R$^1$, R$^2$ and R$^3$ are as defined in the description, and a medicinal product containing the same useful for treating a disorder of the melatoninergic system.

10 Claims, No Drawings

ALKOXYARYL COMPOUNDS

The invention relates to new alkoxyaryl compounds, to their process of preparation and to the pharmaceutical compositions which contain them.

Many studies in the last ten years have demonstrated the fundamental role of melatonin (5-methoxy-N-acetyltryptamine) in controlling the circadian rhythm and endocrine functions, and the melatonin receptors have been characterized and localized.

In addition to their beneficial effect on disorders of the circadian rhythm (J. Neurosurg., 1985, 63, pp 321–341) and sleep disorders (Psychopharmacology, 1990, 100, pp 222–226), ligands for the melatoninergic system have advantageous pharmacological properties as regards the central nervous system, in particular anxiolytic and antipsychotic properties (Neuropharmacology of Pineal Secretions, 1990, 8 (3–4), pp 264–272) and analgesic properties (Pharmacopsychiat., 1987, 20, pp 222–223), and for the treatment of Parkinson's disease (J. Neurosurg., 1985, 63, pp 321–341) and Alzheimer's disease (Brain Research, 1990, 528, pp 170–174). These compounds have likewise shown activity against certain cancers (Melatonin - Clinical Perspectives, Oxford University Press, 1988, page 164–165), on ovulation (Science, 1987, 227, pp 714–720) and against diabetes (Clinical Endocrinology, 1986, 24, pp 359–364).

Compounds which make it possible to act on the melatoninergic system are therefore excellent medicaments which can be used by the clinician in the treatment of pathologies related to the melatoninergic system and in particular those mentioned above.

The Applicant Company has discovered new alkoxyaryl compounds, of novel structure, which show a very high affinity for melatoninergic receptors and which exhibit, in vitro and in vivo, considerable pharmacological and therapeutic advantage.

The invention relates more particularly to the compounds of formula (I):

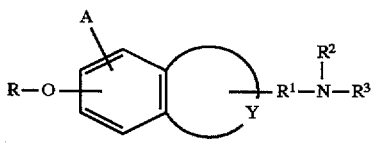

in which:

$R^1$ represents a $(C_1-C_4)$alkylene chain which is unsubstituted or substituted by a radical chosen from alkyl, hydroxyl, alkoxycarbonyl and carboxyl;

$R^2$ represents a hydrogen atom or an alkyl;

$R^3$ represents:
either a group of formula $R^{31}$

in which n represents zero or an integer from 1 to 3, X represents a sulfur or an oxygen and $R^5$ represents a hydrogen atom, an unsubstituted or substituted alkyl, an alkenyl, an alkynyl, an unsubstituted or substituted cycloalkyl or an unsubstituted or substituted dicycloalkylalkyl, or a group of formula $R^{32}$:

in which X' represents an oxygen or sulfur atom, m represents zero or an integer from 1 to 3 and $R^6$ represents a hydrogen, an unsubstituted or substituted alkyl, an alkenyl or an alkynyl, it being understood that $R^6$ may also represent an unsubstituted or substituted cycloalkyl or an unsubstituted or substituted dicycloalkylalkyl when X' is oxygen;

A represents a radical chosen from an alkyl and an A' group chosen from a substituted alkyl, an alkenyl or an alkynyl, R represents a group chosen from an unsubstituted or substituted alkyl, an alkenyl, an alkynyl, an unsubstituted or substituted cycloalkyl, an unsubstituted or substituted cycloalkylalkyl, an unsubstituted or substituted aryl, an unsubstituted or substituted arylalkyl, an unsubstituted or substituted diarylalkyl, a cycloalkenyl and a cycloalkenylalkyl, Y forms, with the benzo ring to which it is bonded, a $Y^1$ group which
either represents a group chosen from naphthalene, benzofuran, benzothiophene and indole, in the case where A represents an A' group,
or represents a naphthalene group, in the case where A represents an alkyl radical, $Y^1$ optionally being partially hydrogenated, it being understood that:

the expression "substituted" relating to the term "alkyl" means that this group is substituted by one or a number of radicals chosen from halogen, hydroxyl and alkoxy, the expression "substituted" relating to the terms "cycloalkyl", "cycloalkylalkyl" and "dicycloalkylalkyl" means that these groups are substituted on the cycloalkyl part by one or a number of groups chosen from halogen, alkyl, alkoxy, hydroxyl and oxo, the expression "substituted" relating to the terms "aryle", "arylalkyl" and "diarylalkyl" means that these groups are substituted on the aromatic ring by one or a number of radicals chosen from halogen, alkyl, alkyl substituted by one or a number of halogens, alkoxy and hydroxyl, the terms "alkyl" and "alkoxy" denote linear or branched radicals containing from 1 to 6 carbon atoms, the terms "alkenyl" and "alkynyl" denote unsaturated linear or branched radicals containing 2 to 6 carbon atoms, the term "cycloalkyl" denotes a saturated cyclic group containing 3 to 8 carbon atoms, the term "cycloalkenyl" denotes an unsaturated cyclic group containing 3 to 8 carbon atoms, the term "aryl" denotes a phenyl or naphthyl group, to their enantiomers and diastereoisomers, and to their addition salts with a pharmaceutically acceptable base.

The invention particularly relates to:
the compounds of formula (I) in which $R^1$ represents an ethylene chain,
the compounds of formula (I) in which $R^2$ represents a hydrogen atom,
the compounds of formula (I) in which $R^3$ represents a group of formula $R^{31}$,
the compounds of formula (I) in which $R^5$ represents an alkyl, the compounds of formula (I) in which $R^5$ represents a cycloalkyl group, the compounds of formula (I) in which $R^3$ represents an $R^{32}$ group, the compounds of formula (I) in which $R^6$ represents an alkyl, the compounds of formula (I) in which $R^6$ represents a cycloalkyl, the compounds of formula (I) in which X is an oxygen atom, the compounds of formula (I) in which X is a sulfur atom, the compounds of formula (I) in which X' is an oxygen atom, the compounds of formula (I) in which X' is a sulfur atom, the compounds of formula (I) in which A is an alkyl radical, the compounds of formula (I) in which A is an A' radical, the compounds of formula (I) in which A' is an alkenyl radical, the compounds of formula (I) in which A' is an alkynyl radical, the compounds of formula (I) in which R is an alkyl radical, the compounds of formula (I) in which R is an alkenyl radical, the compounds of formula (I) in which R is an alkynyl radical, the compounds of formula (I) in which Y forms, with the benzo ring to which it is bonded, a naphthalene group, the compounds of formula (I) in which Y forms, with the benzo ring to which it is bonded, a tetrahydronaphthalene group, the compounds of formula (I) in which Y forms, with the benzo ring to which it is bonded, an indole group, and the compounds of formula (I) in which Y forms, with the benzo ring to which it is bonded, a benzofuran or benzothiophene group.

The invention more particularly relates to:

the compounds of formula ($I_1$)

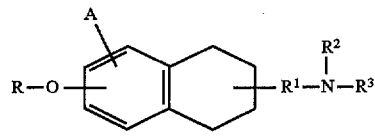

in which A, R, $R^1$, $R^2$ and $R^3$ are as defined in the formula (I), the compounds of formula ($I_2$)

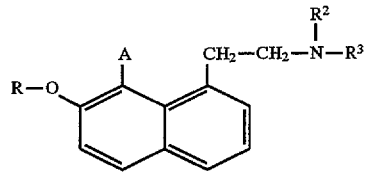

in which A', R, $R^1$, $R^2$ and $R^3$ are as defined in the formula (I), and the compounds of formula ($I_3$):

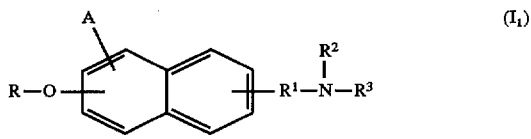

in which A, R, $R^1$, $R^2$ and $R^3$ are as defined in the formula (I).

For example, the invention relates to the compounds of formula ($I_4$):

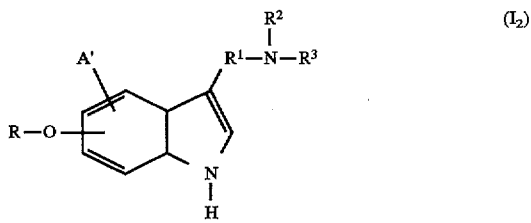

in which A, R, $R^2$ and $R^3$ are as defined in the formula (I), the compounds of formula ($I_5$):

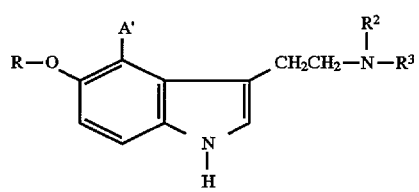

in which A', R, $R^2$ and $R^3$ are as defined in the formula (I), and the compounds of formula ($I_6$):

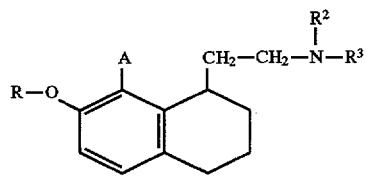

in which A, R, $R^2$ and $R^3$ are as defined in the formula (I).

The alkyl radicals present in the formula (I) can in particular be chosen from methyl, ethyl, n-propyl, isopropyl, n-butyl, isobutyl, sec-butyl, tert-butyl, pentyl and hexyl and the skeletal isomers of the pentyl and hexyl radicals, the alkenyl radicals present in the formula (I) can in particular be chosen from vinyl, allyl, propenyl, butenyl, pentenyl and hexenyl and their isomers according to the position of the double bond, the alkynyl radicals present in the formula (I) can in particular be chosen from ethynyl, propargyl, butynyl, pentynyl and hexynyl and their isomers according to the position of the triple bond, the alkoxy radicals present in the formula (I) can in particular be chosen from methoxy, ethoxy, n-propoxy, isopropoxy, n-butoxy, isobutoxy, sec-butoxy, tert-butoxy, pentyloxy and hexyloxy, and the skeletal isomers of the pentyloxy and hexyloxy radicals, the halogens present in the formula (I) can in particular be chosen from bromine, chlorine, fluorine and iodine, the cycloalkyls present in the formula (I) can in particular be chosen from cyclopropyl, cyclobutyl, cyclopentyl, cyclohexyl, cycloheptyl and cyclooctyl, the cycloalkenyls present in the formula (I) can in particular be chosen from cyclopropenyl, cyclobutenyl, cyclopentenyl, cyclohexenyl, cycloheptenyl and cyclooctenyl, and the alkylene groups present in the formula (I) can in particular be chosen from methylene, ethylene, trimethylene, tetramethylene, pentamethylene and hexamethylene.

Mention may be made, as examples and in a nonlimiting way, among the pharmaceutically acceptable bases which can be used to form an addition salt with the compounds of the invention, of sodium, potassium, calcium or aluminum hydroxides, alkali metal or alkaline-earth metal carbonates and organic bases, such as triethylamine, benzylamine, diethanolamine, tert-butylamine, dicyclohexylamine and arginine.

The invention relates to the process for the preparation of the compounds of formula (I), which comprises the reaction of a compound of formula (II):

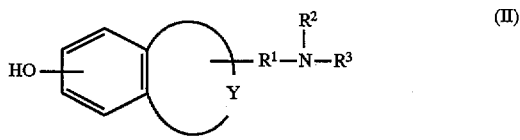

in which $R^1$, $R^2$ and $R^3$ and Y are as defined in the formula (I), with a compound of formula (III/a):

where A has the same definition as in the formula (I) and Z represents a leaving group, for example a halogen atom or a tosyl group, in order to obtain a compound of formula (IV):

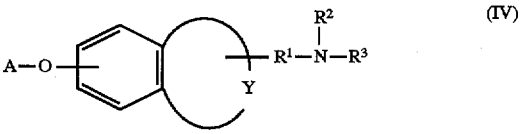

in which A, $R^1$, $R^2$, $R^3$ and Y are as defined above, this compound of formula (IV) undergoing, under reflux, a rearrangement reaction which results in the compound of formula (V):

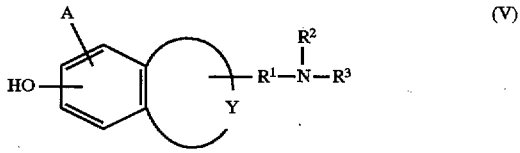

in which A, $R^1$, $R^2$, $R^3$ and Y are as defined above, this compound of formula (V) then being alkylated by a radical of formula R with R as defined in the formula (I), in order to obtain a compound of formula (I):

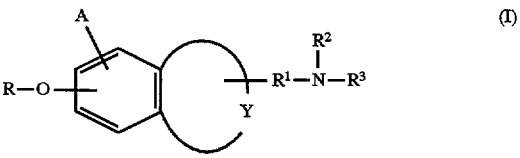

in which A, R, $R^1$, $R^2$, $R^3$ and Y are as defined above, which compounds of formula (I) can be, if desired, purified according to one or a number of purification methods chosen from crystallization, silica gel chromatography, extraction, filtration and passing through charcoal or resin, separated, if appropriate, in the pure form or in the form of a mixture, into their possible enantiomers or diastereoisomers, or salified by a pharmaceutically acceptable base.

Alkylation of the compounds of formula (V) by an R group can be carried out, for example, by virtue of a compound of formula (III/b):

R—Z'  (III/b)

where R has the same definition as in the formula (I) and Z' represents a leaving group, for example a halogen atom or a tosyl group, or by virtue of a dialkyl sulfate.

The invention also relates to a process for the preparation of the compounds of formula (I/a), a specific case of the compounds of formula (I):

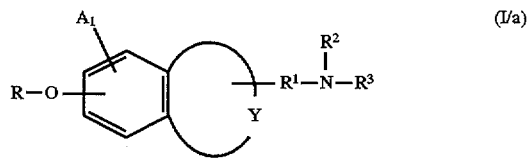

in which Y, R, $R^1$, $R^2$ and $R^3$ are as defined in the formula (I) et $A_1$ is an alkyl radical, which comprises the hydrogenation of a compound of formula (I/b):

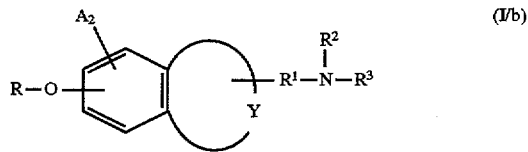

in which Y, R, $R^1$, $R^2$ and $R^3$ are as above and $A_2$ is an alkenyl radical.

The compounds of formula (I) in which Y forms, with the benzo ring to which it is bonded, a di- or tetrahydronaphthalene group can be obtained by hydrogenation of the corresponding compounds of formula (I) in which Y forms, with the benzo ring to which it is bonded, a naphthalene group.

The invention also relates to a process for the preparation of the compounds of formula (I), which comprises the reaction of a compound of formula (VI):

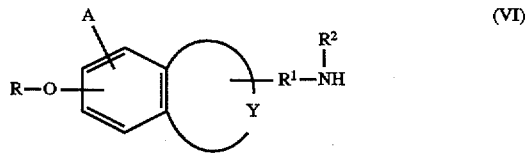

in which A, R, $R^1$, $R^2$ and Y are as defined in the formula (I), a) with an acyl chloride of formula (VII):

in which n and $R^5$ are as defined in the formula (I), or with the corresponding acid anhydride (mixed or symmetrical), b) or alternatively with an iso(thio)cyanate of formula (VIII):

X=C=N—(CH$_2$)$_m$—R$^6$  (VIII)

with X, m and $R^6$ as defined in the formula (I) in order to obtain, respectively:

a) the compound of formula (I/c):

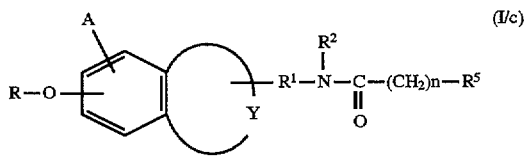

in which A, R, Y, $R^1$, $R^2$, $R^5$ and n are as defined above, or b) the compound of formula (I/d):

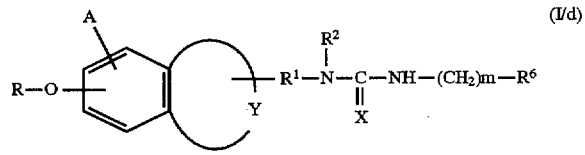

in which A, R, Y, $R^1$, $R^2$, $R^6$, X and m are as defined above, it being possible for the compound of formula (I/c) to be subjected to a thionation agent, such as Lawesson's reagent, in order to obtain the compounds of formula (I/e):

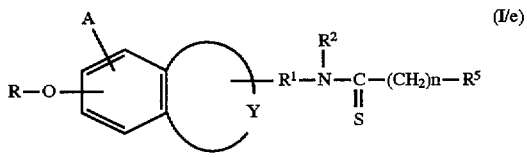

in which A, R, Y, $R^1$, $R^2$, $R^5$ and m are as defined above, the compounds of formula (I/c), (I/d) and (I/e) forming the group of the compounds of formula (I),
it being possible for the compounds of formula (I) to be, if desired, purified according to one or a number of purification methods chosen from crystallization, silica gel chromatography, extraction, filtration and passing through charcoal or resin, separated, if appropriate, in the pure form or in the form of a mixture, into their possible enantiomers or diastereoisomers, or salified by a pharmaceutically acceptable base.

The starting materials used in the processes described above are either commercially available or known in the state of the art or are easily accessible to a person skilled in the art according to processes which are well known in the literature. More specific reference will be made, for the compounds of general formula (II), to the descriptions of Patent EP 447,285 and of Patent Application EP 530,087, incorporated by reference.

The compounds of formula (I) have pharmacological properties which are of great interest to the clinician.

The compounds of the invention and the pharmaceutical compositions containing them are proving to be useful in the treatment of disorders of the melatoninergic system and disorders related to the melatoninergic system.

The pharmacological study of the compounds of the invention has in fact shown that they were not toxic, that they had a very high selective affinity for melatonin receptors and that they had significant activities with respect to the central nervous system and, in particular, therapeutic properties with respect to sleep disorders, anxiolytic, antipsychotic and analgesic properties and properties with respect to the microcirculation were noted, which make it possible to establish that the products of the invention are useful in the treatment of stress, sleep disorders, anxiety, seasonal depressions, cardiovascular pathologies, insomnia and tiredness due to jet lag, schizophrenia, panic attacks, melancholia, eating disorders, obesity, psoriasis, psychotic disorders, epilepsy, Parkinson's disease, senile dementia, various disorders related to normal or pathological ageing, migrane, memory losses, Alzheimer's disease and disorders of cerebral circulation. In another field of activity, it appears that the products of the invention have ovulation-inhibiting and immunomodulating properties and that they are capable of being used in anticancer treatment.

The compounds will preferably be used in the treatment of seasonal depressions, sleep disorders, cardiovascular pathologies, insomnia and tiredness due to jet lag, eating disorders and obesity.

For example, the compounds will be used in the treatment of seasonal depressions and sleep disorders.

Another subject of the present invention is the pharmaceutical compositions containing the products of formula (I) or, if appropriate, one of their addition salts with a pharmaceutically acceptable base in combination with one or a number of pharmaceutically acceptable excipients.

Mention can more particularly be made, among the pharmaceutical compositions according to the invention, of those which are suitable for oral, parenteral, nasal, per- or transcutaneous, rectal, perlingual, ocular or respiratory administration and in particular simple or sugar-coated tablets, sublingual tablets, chartulas, packets, gelatin capsules, glossettes, lozenges, suppositories, creams, ointments, dermal gels and imbibable or injectable phials.

The dosage varies according to the age and weight of the patient, the administration route, the nature of the therapeutic indication or possible associated treatments and ranges between 0.1 mg and 1 g per 24 hours in 1 or 2 administrations and more particularly 1 to 100 mg, for example 1 to 10 mg.

The following examples illustrate the invention but do not limit it in any way.

PREPARATION 1: N-[2-(7-HYDROXYNAPHTH-1-YL)ETHYL]ACETAMIDE

Stage A: 2-(7-HYDROXYNAPHTH-1-YL)ETHYLAMINE HYDROBROMIDE

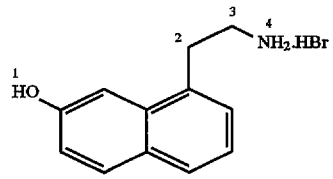

Reactants:

2-(7-Methoxynaphth-1-yl)ethylamine hydrochloride: 58 mmol (13.8 g)

47% Aqueous HBr solution: 390 mmol (46 cm$^3$)

Procedure:

The ethylamine hydrochloride and the 47% HBr solution are introduced into a 250 cm$^3$ round-bottomed flask. The mixture is brought to reflux for 5 hours. After cooling, the reaction mixture is filtered.

Characteristics:

Molecular mass: 268.16 g for $C_{12}H_{14}BrNO$

Appearance: white solid

Melting point: 174°–175° C.

$R_f$: 0.72 eluent: Methanol/28% Aqueous ammonia (4/1)

Yield: 80%

Recrystallization solvent: ethyl acetate/hexane (1–3)

| Spectroscopic analysis in the infra red: | | |
|---|---|---|
| 3240–3460 | cm$^{-1}$ | ν OH |
| 3040–3100 | cm$^{-1}$ | ν C=C twisting |
| 2950–3060 | cm$^{-1}$ | ν CH |
| 2480–2720 | cm$^{-1}$ | ν NH$_{3+}$ |

NMR spectroscopic analysis (80 MHz, d$_6$-DMSO, δ):

| 3.0–3.4 | ppm | unresolved peak | 4H | H2, H3 |
|---|---|---|---|---|
| 7.0–7.9 | ppm | unresolved peak | 6H | aromatic H |
| 8.1 | ppm | singlet | 3H | H4 |
| 9.8 | ppm | singlet | 1H | H1 |

| Elemental analysis: | | | |
|---|---|---|---|
| | % C | % H | % N |
| Calculated: | 53.75 | 5.26 | 5.22 |
| Found: | 53.84 | 5.30 | 5.32 |

Stage B: N-[2-(7-HYDROXYNAPHTH-1-YL)ETHYL] ACETAMIDE

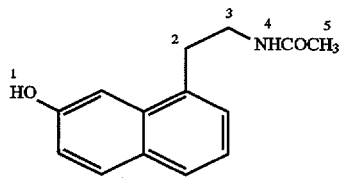

Reactants:
2-(7-Hydroxynaphth-1-yl)ethylamine hydrobromide: 3.8 mmol (1.02 g)
Sodium carbonate: 8.5 mmol (0.90 g)
Acetyl chloride: 3.8 mmol (0.30 g)
Procedure:

The sodium carbonate is dissolved in 5 cm$^3$ of water in a 50 cm$^3$ flask and the hydrobromide is added with stirring. 20 cm$^3$ of ethyl acetate are added to the suspension obtained and then the acetyl chloride is poured in dropwise. Stirring is maintained for 30 minutes (the solution is clear). The organic phase is extracted with water, then with a 1N aqueous HCl solution and then with water until the wash liquors are neutral. The organic phase is dried over magnesium sulfate, filtered and dried under reduced pressure.
Characteristics:
Molecular mass: 229.27 g for C$_{14}$H$_{15}$NO$_2$
Appearance: white solid
Melting point: 125°–126° C.
R$_f$: 0.32 eluent: Acetone:Foluene/Cyclohexane (4/4/2)
Yield: 60%
Recrystallization solvent: water

| Spectroscopic analysis in the infra red: | | |
|---|---|---|
| 3340 | cm$^{-1}$ | ν OH |
| 2980 | cm$^{-1}$ | ν CH |
| 1640 | cm$^{-1}$ | ν CO amide |

| NMR spectroscopic analysis (80 MHz, CDCl$_3$, δ): | | | | |
|---|---|---|---|---|
| 2.0 | ppm | singlet | 3H | H5 |
| 3.2 | ppm | triplet | 2H | H2 J2–3 = 7.1 Hz |
| 3.6 | ppm | multiplet | 2H | H3 |
| 5.8 | ppm | signal | 1H | H4 |
| 7.0–7.9 | ppm | unresolved peak | 6H | aromatic H |
| 9.8 | ppm | singlet | 1H | H1 |

| Elemental analysis: | | | |
|---|---|---|---|
| | % C | % H | % N |
| Calculated: | 73.34 | 6.59 | 6.11 |
| Found: | 72.99 | 6.57 | 6.29 |

PREPARATIONS 2 TO 10:

By carrying out the synthesis in a way analogous to that described for Preparation 1 but using either the appropriate acyl chloride or the appropriate acid anhydride, the following preparations are obtained:
PREPARATION 2: N-[2-(7-HYDROXYNAPHTH-1-YL)ETHYL]FORMAMIDE
PREPARATION 3: N-[2-(7-HYDROXYNAPHTH-1-YL)ETHYL]PROPIONAMIDE
PREPARATION 4: N-[2-(7-HYDROXYNAPHTH-1-YL)ETHYL]BUTYRAMIDE
PREPARATION 5: N-[2-(7-HYDROXYNAPHTH-1-YL)ETHYL]PENTANAMIDE
PREPARATION 6: N-[2-(7-HYDROXYNAPHTH-1-YL)ETHYL]HEXANAMIDE
PREPARATION 7: N-[2-(7-HYDROXYNAPHTH-1-YL)ETHYL]HEPTANAMIDE
PREPARATION 8: N-[2-(7-HYDROXYNAPHTH-1-YL)ETHYL]CYCLOPROPANECARBOXAMIDE
PREPARATION 9: N-[2-(7-HYDROXYNAPHTH-1-YL)ETHYL]CYCLOBUTANECARBOXAMIDE
PREPARATION 10: N-[2-(7-HYDROXYNAPHTH-1-YL)ETHYL]TRIFLUOROACETAMIDE
PREPARATION 11: N-[2-(7-HYDROXYNAPHTH-1-YL)ETHYL]IODOACETAMIDE
PREPARATION 12: N-[2-(7-HYDROXYNAPHTH-1-YL)ETHYL]-N'-METHYLUREA The title compound is obtained by reacting 2-(7-methoxynaphth-1-yl)ethylamine hydrochloride with methyl isocyanate.

PREPARATIONS 13 TO 30:

By carrying out the synthesis as in Preparation 12 but using the appropriate is(thio)cyanate, the following compounds are obtained:
PREPARATION 13: N-[2-(7-HYDROXYNAPHTH-1-YL)ETHYL]UREA
PREPARATION 14: N-[2-(7-HYDROXYNAPHTH-1-YL)ETHYL]-N'-ETHYLUREA
PREPARATION 15: N-[2-(7-HYDROXYNAPHTH-1-YL)ETHYL]-N'-PROPYLUREA
PREPARATION 16: N-[2-(7-HYDROXYNAPHTH-1-YL)ETHYL]-N'-BUTYLUREA
PREPARATION 17: N-[2-(7-HYDROXYNAPHTH-1-YL)ETHYL]-N'-PENTYLUREA
PREPARATION 18: N-[2-(7-HYDROXYNAPHTH-1-YL)ETHYL]-N'-HEXYLUREA
PREPARATION 19: N-[2-(7-HYDROXYNAPHTH-1-YL)ETHYL]-N'-CYCLOPROPYLUREA
PREPARATION 20: N-[2-(7-HYDROXYNAPHTH-1-YL)ETHYL]-N'-CYCLOBUTYLUREA
PREPARATION 21: N-[2-(7-HYDP-OXYNAPHTH-1-YL)ETHYL]-N'-CYCLOHEXYLUREA
PREPARATION 22: N-[2-(7-HYDROXYNAPHTH-1-YL)ETHYL]THIOUREA
PREPARATION 23: N-[2-(7-HYDROXYNAPHTH-1-YL)ETHYL]-N'-METHYLTHIOUREA

PREPARATION 24: N-[2-(7-HYDROXYNAPHTH-1-YL) ETHYL]-N'-ETHYLTHIOUREA

PREPARATION 25: N-[2-(7-HYDROXYNAPHTH-1-YL) ETHYL]-N'-PROPYLTHIOUREA

PREPARATION 26: N-[2-(7-HYDROXYNAPHTH-1-YL) ETHYL]-N'-BUTYLTHIOUREA

PREPARATION 27: N-[2-(7-HYDROXYNAPHTH-1-YL) ETHYL]-N'-PENTYLTHIOUREA

PREPARATION 28: N-[2-(7-HYDROXYNAPHTH-1-YL) ETHYL]-N'-HEXYLTHIOUREA

PREPARATION 29: N-[2-(7-HYDROXYNAPHTH-1-YL) ETHYL]-N'-ISOPROPYLTHIOUREA

PREPARATION 30: N-[2-(7-HYDROXYNAPHTH-1-YL) ETHYL]-N'-ISOBUTYLTHIOUREA

PREPARATION 31: N-[2-(5-HYDROXYINDOL-3-YL) ETHYL]ACETAMIDE (J. Med. Chem., 1994, 37, pp 2828–2830)

PREPARATION 32: N-[2-(5-HYDROXYBENZOFUR-3-YL)ETHYL]ACETAMIDE

PREPARATION 33: N-[2-(5-HYDROXYBENZOTHIOPHEN-3-YL)ETHYL]ACETAMIDE (J. Med. Chem., 1970, 13, pp 1205–1208)

EXAMPLE 1: N-[2-(7-METHOXY-8-ALLYLNAPHTH-1-YL) ETHYL]ACETAMIDE

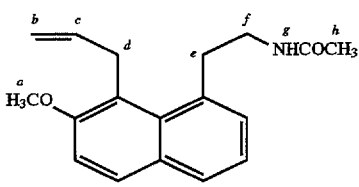

Stage A: N-[2-(7-ALLYLOXYNAPHTH-1-YL) ETHYL] ACETAMIDE

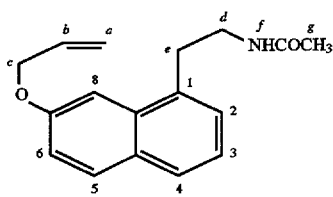

Reactants:

N-[2-(7-Hydroxynaphth-1-yl)ethyl]acetamide: 20 mmol (5 g)

Potassium carbonate: 50 mmol (6.91 g)

Allyl bromide: 30 mmol (3.63 g)

Procedure:

The compound obtained in Preparation 1 is dissolved in 100 cm³ of anhydrous acetone. The potassium carbonate is added and the reaction mixture is left stirring at reflux for 30 minutes. The allyl bromide is added dropwise. The reaction mixture is left at reflux and with stirring for 3 hours. After cooling, the reaction mixture is filtered and the filtrate is dried under reduced pressure. The oil obtained is purified by column chromatography.

Characteristics:

Molecular mass: 269.33 g for $C_{17}H_{19}NO_2$

Appearance: oil $R_f$: 0.19 eluent: Acetone/Toluene/Cyclohexane (2/3/5)
Yield: 87%

| Spectroscopic analysis in the infrared: | | |
|---|---|---|
| 3260 | cm⁻¹ | ν NH amide |
| 2920–2840 | cm⁻¹ | ν CH |
| 1635 | cm⁻¹ | ν CO amide |
| 1590 | cm⁻¹ | ν C=C |

NMR Spectroscopic analysis (300 MHz, CDCl₃, δ):

| | | | | |
|---|---|---|---|---|
| 1.90 | ppm | singlet | 3H Hg | |
| 3.20 | ppm | triplet | 2H He | $J_{e-d} = 7.0$ Hz |
| 3.60 | ppm | multiplet | 2H Hd | |
| 4.70 | ppm | doublet | 2H Hc | $J_{c-b} = 5.3$ Hz |
| 5.30 | ppm | doublet | 1H Ha cis | $J_{a-b} = 10.5$ Hz |
| 5.50 | ppm | doublet | 1H Ha trans | $J_{a-b} = 17.3$ Hz |
| 5.60 | ppm | signal | 1H Hf | |
| 6.15 | ppm | multiplet | 1H Hb | |
| 7.15 | ppm | double doublet | 1H H6 | $J_{ortho} = 8.9$ Hz; $J_{meta} = 2.3$ Hz |
| 7.18–7.22 | ppm | unresolved peak | 2H H2,3 | |
| 7.40 | ppm | doublet | 1H H8 | $J_{meta} = 2.3$ Hz |
| 7.65 | ppm | multiplet | 1H H4 | |
| 7.75 | ppm | doublet | 1H H5 | $J_{ortho} = 8.9$ Hz |

| Elemental analysis: | | | |
|---|---|---|---|
| | % C | % H | % N |
| Calculated: | 75.80 | 7.11 | 5.20 |
| Found: | 75.75 | 7.15 | 5.20 |

Stage B: N-[2-(7-HYDROXY-8-ALLYLNAPHTH-1-YL) ETHYL]ACETAMIDE

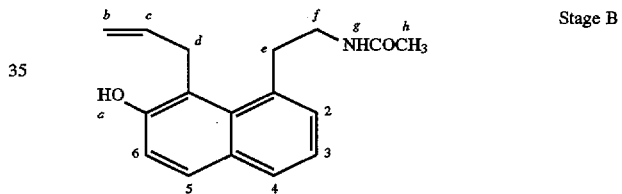

Stage B

Reactants:

N-[2-(7-Allyloxynaphth-1-yl)ethyl]acetamide: 7.4 mmol (2 g)

N,N-Dimethylaniline: 7.4 mmol (10 cm³)

Procedure:

The N-[2-(7-allyloxynaphth-1-yl)ethyl]acetamide is dissolved in the N,N-dimethylaniline and the reaction mixture is brought to reflux (200° C.) for 2 hours. After cooling, 20 cm³ of ether are added and the organic phase is extracted with a 10% aqueous sodium hydroxide solution and then with water. The aqueous phase is then acidified with a 6N aqueous HCl solution and left stirring for a few minutes. The precipitate obtained is filtered off.

Characteristics:

Molecular mass: 269.33 g for $C_{17}H_{19}NO_2$

Appearance: pale-yellow solid

Melting temperature: 157°–159° C.

$R_f$: 0.38 eluent: Acetone/Toluene/Cyclohexane (4/4/2)
Yield: 84%

Recrystallization solvent: cyclohexane

| Spectroscopic analysis in the infrared: | | |
|---|---|---|
| 3280 | cm⁻¹ | ν NH amide |
| 2860–3000 | cm⁻¹ | ν CH |
| 1600 | cm⁻¹ | ν CO amide |

-continued

NMR spectroscopic analysis (300 MHz, $d_6$-DMSO, δ):

| 1.83 | ppm | singlet | 3H | Hh | |
|---|---|---|---|---|---|
| 3.20 | ppm | signal | 2H | He | |
| 3.25 | ppm | signal | 2H | Hf | |
| 3.90 | ppm | signal | 2H | Hd | |
| 4.65 | ppm | doublet | 1H | Hb trans | $J_{b-c}$ = 17.2 Hz |
| 4.95 | ppm | doublet | 1H | Hb cis | $J_{b-c}$ = 8.8 Hz |
| 6.05 | ppm | multiplet | 1H | Hc | |
| 7.14–7.23 | unresolved peak | | 3H | H 2, 3, 6 | |
| 7.64–7.68 | unresolved peak 2H | | H 4,5 | | |
| 8.08 | ppm | signal | 1H | Hg | |
| 9.60 | ppm | singlet | 1H | Ha, exchangeable in $D_2O$ | |

Elemental analysis:

| | % C | % H | % N |
|---|---|---|---|
| Calculated: | 75.81 | 7.11 | 5.20 |
| Found: | 75.72 | 7.09 | 5.31 |

Stage C: N-[2-(7-METHOXY-8-ALLYLNAPHTH-1-YL) ETHYL]ACETAMIDE

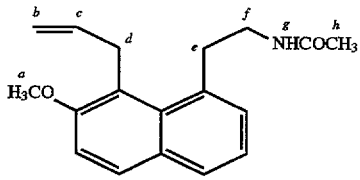

Reagents:
N-[2-(7-Hydroxy-8-allylnaphth-1-yl)ethyl]acetamide: $4 \times 10^3$ mol (1 g)
10% Aqueous sodium hydroxide solution: 0.08 mol (32 $cm^3$)
Dimethyl sulfate: 0.08 mol (7.6 $cm^3$)
Procedure:
The N-[2-(7-hydroxy-8-allylnaphth-1-yl)ethyl]acetamide is dissolved in the aqueous sodium hydroxide solution at 50° C. Heating is halted after 10 minutes and the reaction mixture is left to cool with stirring and the dimethyl sulfate is then added dropwise. The aqueous phase is extracted with 3 times 20 $cm^3$ of ether and the organic phase is washed with a 10% aqueous potassium carbonate solution and then with water until the wash liquors are neutral. The organic phase is dried over $MgSO_4$, filtered and evaporated under vacuum.
Characteristics:
283.37 g/mol for $C_{18}H_{21}NO_2$
Appearance: off-white solid
Melting temperature: 98°–99° C.
$R_f$: 0.38 eluent: Acetone/Toluene/Cyclohexane (4/4/2)
Yield: 81%
Recrystallization solvent: toluene/cyclohexane (1/5)
Spectroscopic analysis in the infrared:
3260 and 3060 $cm^{-1}$: νNH amide
3000–2820 $cm^{-1}$: νCH
1630 $cm^1$: νCO amide
1610 and 1590 $cm^{-1}$: νC=C
1250 $cm^{-1}$: ν$CH_3$O NMR spectroscopic analysis (300 MHz, $CDCl_3$, δ):

| 1.94 | ppm | singlet | 3H | Hh | |
|---|---|---|---|---|---|
| 3.37 | ppm | triplet | 2H | He | $J_{e-f}$ = 7.1 Hz |
| 3.54 | ppm | multiplet | 2H | Hf | |
| 3.94 | ppm | singlet | 3H | Ha | |
| 3.98 | ppm | doublet | 2H | Hd | $J_{d-c}$ = 4.6 Hz |
| 4.73 | ppm | doublet | 1H | Hb trans | $J_{b-c}$ = 17.3 Hz |
| 5.02 | ppm | doublet | 1H | Hb cis | $J_{b-c}$ = 10.2 Hz |
| 5.50 | ppm | signal | 1H | Hg | |
| 6.15 | ppm | multiplet | 1H | Hc | |
| 7.21–7.33 | ppm | unresolved peak | 3H | H2,3,6 | |
| 7.69 | ppm | doublet | 1H | H4 | $J_{ortho}$ = 7.4 Hz |
| 7.79 | ppm | doublet | 1H | H5 | $J_{ortho}$ = 9.0 Hz |

Elemental analysis:

| | % C | % H | % N |
|---|---|---|---|
| Calculated: | 76.30 | 7.47 | 4.94 |
| Found: | 76.51 | 7.64 | 5.21 |

EXAMPLES 2 TO 14:

By carrying out the synthesis as in Example 1 but substituting the hydroxyl functional group by the appropriate radical, the compounds of the following examples are obtained:

EXAMPLE 2: N-[2-(7-ETHOXY-8-ALLYLNAPHTH-1-YL)ETHYL]ACETAMIDE

EXAMPLE 3: N-[2-(7-PROPOXY-8-ALLYLNAPHTH-1-YL)ETHYL]ACETAMIDE melting point: 130°–131° C.

EXAMPLE 4: N-[2-(7-BUTYLOXY-8-ALLYLNAPHTH-1-YL)ETHYL]ACETAMIDE

EXAMPLE 5: N-[2-(7-PENTYLOXY-8-ALLYLNAPHTH-1-YL)ETHYL]ACETAMIDE

EXAMPLE 6: N-[2-(7-HEXYLOXY-8-ALLYLNAPHTH-1-YL) ETHYL]ACETAMIDE

EXAMPLE 7: N-[2-(7-CYCLOPROPYLMETHOXY-8-ALLYLNAPHTH-1-YL)ETHYL]-ACETAMIDE

EXAMPLE 8: N-[2-(7-CYCLOHEXYLOXY-8-ALLYLNAPHTH-1-YL)ETHYL]ACETAMIDE

EXAMPLE 9: N-[2-(7-ALLYLOXY-8-ALLYLNAPHTH-1-YL)ETHYL]ACETAMIDE

EXAMPLE 10: N-[2-(7-VINYLOXY-8-ALLYLNAPHTH-1-YL) ETHYL]ACETAMIDE

EXAMPLE 11: N-[2-(7-PROPARGYLOXY-8-ALLYLNAPHTH-1-YL)ETHYL]ACETAMIDE

EXAMPLE 12: N-[2-(7-BENZYLOXY-8-ALLYLNAPHTH-1-YL) ETHYL]ACETAMIDE

EXAMPLE 13: N-[2-(7-BENZHYDRYLOXY-8-ALLYLNAPHTH-1-YL)ETHYL]ACETAMIDE

EXAMPLE 14: N-[2-(7-CYCLOHEXEN-3-YLOXY-8-ALLYLNAPHTH-1-YL)ETHYL]-ACETAMIDE

EXAMPLES 15 TO 46:

By carrying out the synthesis as in Example 1 but using the appropriate preparations, the compounds of the following examples are obtained:

EXAMPLE 15: N-[2-(7-METHOXY-8-ALLYLNAPHTH-1-YL)ETHYL]FORMAMIDE

EXAMPLE 16: N-[2-(7-METHOXY-8-ALLYLNAPHTH-1-YL)ETHYL]PROPIONAMIDE Melting point: 90°–92° C.

EXAMPLE 17: N-[2-(7-METHOXY-8-ALLYLNAPHTH-1-YL)ETHYL]BUTYRAMIDE Melting point: 75°–77° C.

EXAMPLE 18: N-[2-(7-METHOXY-8-ALLYLNAPHTH-1-YL) ETHYL]PENTANAMIDE Melting point: 60°–62° C.

EXAMPLE 19: N-[2-(7-METHOXY-8-ALLYLNAPHTH-1-YL)ETHYL]HEXANAMIDE

EXAMPLE 20: N-[2-(7-METHOXY-8-ALLYLNAPHTH-1-YL)ETHYL]HEPTANAMIDE

EXAMPLE 21: N-[2-(7-METHOXY-8-ALLYLNAPHTH-1-YL)ETHYL]CYCLOPROPANECARBOXAMIDE Melting point: 112°–114° C.

EXAMPLE 22: N-[2-(7-METHOXY-8-ALLYLNAPHTH-1-YL)ETHYL]CYCLOBUTANECARBOXAMIDE
Melting point: 92°–96° C.
EXAMPLE 23: N-[2-(7-METHOXY-8-ALLYLNAPHTH-1-YL)ETHYL]TRIFLUOROACETAMIDE
EXAMPLE 24: N-[2-(7-METHOXY-8-ALLYLNAPHTH-1-YL)ETHYL]IODOACETAMIDE
EXAMPLE 25: N-[2-(7-METHOXY-8-ALLYLNAPHTH-1-YL)ETHYL]-N'-METHYLUREA
EXAMPLE 26: N-[2-(7-METHOXY-8-ALLYLNAPHTH-1-YL)ETHYL]UREA
EXAMPLE 27: N-[2-(7-METHOXY-8-ALLYLNAPHTH-1-YL)ETHYL]-N'-ETHYLUREA
EXAMPLE 28: N-[2-(7-METHOXY-8-ALLYLNAPHTH-1-YL)ETHYL]-N'-PROPYLUREA
EXAMPLE 29: N-[2-(7-METHOXY-8-ALLYLNAPHTH-1-YL)ETHYL]-N'-BUTYLUREA
EXAMPLE 30: N-[2-(7-METHOXY-8-ALLYLNAPHTH-1-YL)ETHYL]-N'-PENTYLUREA
EXAMPLE 31: N-[2-(7-METHOXY-8-ALLYLNAPHTH-1-YL)ETHYL]-N'-HEXYLUREA
EXAMPLE 32: N-[2-(7-METHOXY-8-ALLYLNAPHTH-1-YL) ETHYL]-N'-CYCLOPROPYLUREA
EXAMPLE 33: N-[2-(7-METHOXY-8-ALLYLNAPHTH-1-YL) ETHYL]-N'-CYCLOBUTYLUREA
EXAMPLE 34: N-[2-(7-METHOXY-8-ALLYLNAPHTH-1-YL)ETHYL]-N'-CYCLOHEXYLUREA
EXAMPLE 35: N-[2-(7-METHOXY-8-ALLYLNAPHTH-1-YL) ETHYL]THIOUREA
EXAMPLE 36: N-[2-(7-METHOXY-8-ALLYLNAPHTH-1-YL) ETHYL]-N'-METHYLTHIOUREA
EXAMPLE 37: N-[2-(7-METHOXY-8-ALLYLNAPHTH-1-YL)ETHYL]-N'-ETHYLTHIOUREA
EXAMPLE 38: N-[2-(7-METHOXY-8-ALLYLNAPHTH-1-YL)ETHYL]-N'-PROPYLTHIOUREA
EXAMPLE 39: N-[2-(7-METHOXY-8-ALLYLNAPHTH-1-YL)ETHYL]-N'-BUTYLTHIOUREA
EXAMPLE 40: N-[2-(7-METHOXY-8-ALLYLNAPHTH-1-YL)ETHYL]-N'-PENTYLTHIOUREA
EXAMPLE 41: N-[2-(7-METHOXY-8-ALLYLNAPHTH-1-YL)ETHYL]-N'-HEXYLTHIOUREA
EXAMPLE 42: N-[2-(7-METHOXY-8-ALLYLNAPHTH-1-YL)ETHYL]-N'-ISOPROPYLTHIOUREA
EXAMPLE 43: N-[2-(7-METHOXY-8-ALLYLNAPHTH-1-YL)ETHYL]-N'-ISOBUTYLTHIOUREA
EXAMPLE 44: N-[2-(5-METHOXY 4-ALLYLINDOL-3-YL)ETHYL]ACETAMIDE
EXAMPLE 45: N-[2-(5-METHOXY 4-ALLYLBENZOFUR-3-YL)ETHYL]ACETAMIDE
EXAMPLE 46: N-[2-(5-METHOXY 4-ALLYLBENZOTHIOPHEN-3-YL)ETHYL]-ACETAMIDE

EXAMPLES 47 TO 54:

By carrying out the synthesis as in Example 1 but using the appropriate reactants of formula (III/a), the compounds of the following examples are obtained:
EXAMPLE 47: N-[2-(7-METHOXY-8-VINYLNAPHTH-1-YL)ETHYL]ACETAMIDE
EXAMPLE 48: N-[2-(7-M ETHOXY-8-(PROP-1-EN-1-YL)NAPHTH-1-YL)ETHYL]-ACETAMIDE
EXAMPLE 49: N-[2-(7-METHOXY-8-ISOPROPENYLNAPHTH-1-YL)ETHYL]-ACETAMIDE
EXAMPLE 50: N-[2-(7-METHOXY-8-(BUT-2-EN-1-YL) NAPHTH-1-YL)ETHYL]ACETAMIDE
EXAMPLE 51: N-[2-(7-METHOXY-8-(BUT-3-EN-1-YL) NAPHTH-1-YL)ETHYL]ACETAMIDE
EXAMPLE 52: N-[2-(7-METHOXY-8-(PENT-4-EN-1-YL) NAPHTH-1-YL)ETHYL]-ACETAMIDE
EXAMPLE 53: N-[2-(7-METHOXY-8-(HEX-5-EN-1-YL) NAPHTH-1-YL) ETHYL]ACETAMIDE
EXAMPLE 54: N-[2-(7-METHOXY-8-PROPARGYLNAPHTH-1-YL)ETHYL]ACETAMIDE
EXAMPLE 55: N-[2-(7-METHOXY-8-PROPYLNAPHTH-1-YL)ETHYL]ACETAMIDE

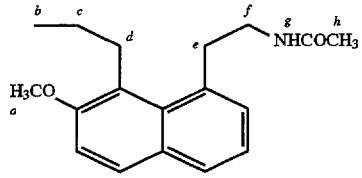

Reactants:
N-[2-(7-Methoxy-8-allylnaphth-1-yl)ethyl]acetamide: 0.8 g ($2.8 \times 10^{-3}$ mol)
98% Hydrazine: 0.41 cm$^3$ ($8.4 \times 10^{-3}$ mol)
Copper sulfate: 0.05 g ($2.8 \times 10^{-4}$ mol)
95° Ethanol: 20 cm$^3$ Procedure:

The N-[2-(7-methoxy-8-allylnaphth-1-yl)ethyl]acetamide (Example 1) is introduced into 20 cm$^3$ of ethanol in a 100 cm$^3$ two-necked flask and air (containing O$_2$) is bubbled into the reaction mixture. The hydrazine and the copper sulfate are added with stirring and under air. The reaction mixture is left stirring for 48 hours. The reaction mixture is filtered and the filtrate is evaporated. The residue is taken up in 20 cm$^3$ of ether and the organic phase is washed with a 2N aqueous HCl solution and then with water until the wash liquors are neutral. The organic phase is dried over CaCl$_2$, filtered and evaporated.

Characteristics:
285.39 g/mol for C$_{18}$H$_{23}$NO$_2$
Appearance: white solid
Melting temperature: 103°–105° C.
R$_f$: 0.39 eluent: Acetone/Toluene/Cyclohexane (4/4/2)
Yield: 45%
Recrystallization solvent: alcohol/water (3/1)
Spectroscopic analysis in the infrared:
3300 and 3030 cm$^{-1}$: vNH amide
3000–2820 cm$^{-1}$: vCH
1660 cm$^{-1}$: vCO amide
1600 and 1590 cm$^{-1}$: vC═C
1250 cm$^{-1}$: vCH$_3$O

| NMR spectroscopic analysis (80 MHz, CDCl$_3$, δ): | | | | | |
|---|---|---|---|---|---|
| 1.00 | ppm | triplet | 3H | Hb | J$_{b-c}$ = 6.80 Hz |
| 1.60 | ppm | multiplet | 2H | Hc | |
| 1.95 | ppm | singlet | 3H | Hh | |
| 3.00–3.65 | ppm | unresolved peak | 6H | He,d,f | |
| 3.95 | ppm | singlet | 3H | Ha | |
| 5.40 | ppm | signal | 1H | Hg | |
| 7.20–7.35 | ppm | unresolved peak | 3H | H2,3,6 | |
| 7.60–7.80 | ppm | unresolved peak | 2H | H4,5 | |

| Elemental analysis: | | | |
|---|---|---|---|
| | % C | % H | % N |
| Calculated: | 75.76 | 8.12 | 4.91 |
| Found: | 75.72 | 8.02 | 4.91 |

EXAMPLES 56 TO 60:

By carrying out the synthesis as in Example 55 but starting from the compounds of the appropriate examples, the compounds of the following examples are obtained:

EXAMPLE 56: N-[2-(7-METHOXY-8-ETHYLNAPHTH-1-YL)ETHYL]ACETAMIDE
EXAMPLE 57: N-[2-(7-METHOXY-8-ISOPROPYLNAPHTH-1-YL)ETHYL]ACETAMIDE
EXAMPLE 58: N-[2-(7-METHOXY-8-BUTYLNAPHTH-1-YL)ETHYL]ACETAMIDE
EXAMPLE 59: N-[2-(7-METHOXY-8-PENTYLNAPHTH-1-YL)ETHYL]ACETAMIDE
EXAMPLE 60: N-[2-(7-METHOXY-8-HEXYLNAPHTH-1-YL)ETHYL]ACETAMIDE
EXAMPLE 61: N-[2-(7-METHOXY-8-PROPYL-1,2,3,4-TETRAHYDRONAPHTH-1-YL)-ETHYL]ACETAMIDE

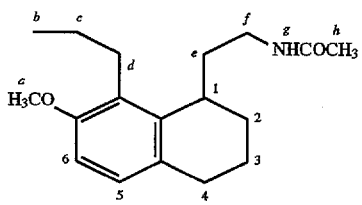

Reactants:
N-[2-(7-Methoxy-8-allylnaphth-1-yl)ethyl]acetamide: 1 g ($3.5 \times 10^{-3}$ mol)
Pd/C: 1 g
95° Ethanol: 20 cm$^3$
Procedure:
The N-[2-(7-methoxy-8-allylnaphth-1-yl)ethyl]acetamide (Example 1) is dissolved in the ethanol, the palladium-on-charcoal (Pd/C) is added and the reaction mixture is stirred under H$_2$ at atmospheric pressure and room temperature. The reaction is completed after 3 hours, the reaction mixture is filtered and the filtrate is evaporated. The solid obtained is recrystallized.
Characteristics:
289.42 g/mol for $C_{18}H_{27}NO_2$
Appearance: white solid
Melting point: 110°–112° C.
R$_f$: 0.15 eluent: Acetone/Toluene/Cyclohexane (2/3/5)
Yield: 87%
Recrystallization solvent: alcohol/water (1/5)
Spectroscopic analysis in the infrared:
3260 and 3080 cm$^{-1}$: νNH amide
3000–2820 cm$^{-1}$: νCH
1640 cm$^{-1}$: νCO amide
1250 cm$^{-1}$: νCH$_3$O NMR spectroscopic analysis (80 MHz, CDCl$_3$, δ):

| | | | | | |
|---|---|---|---|---|---|
| 1.00 | ppm | triplet | 3H | Hb | $J_{b-c} = 7.30$ Hz |
| 1.20–1.90 | ppm | unresolved peak | 8H | Hc,e,2 and 3 | |
| 2.00 | ppm | singlet | 3H | Hh | |
| 2.20–2.60 | ppm | unresolved peak | 1H | H1 | |
| 2.60–3.10 | ppm | unresolved peak | 4H | Hd,4 | |
| 3.20–3.55 | ppm | unresolved peak | 2H | Hf | |
| 3.80 | ppm | singlet | 3H | Ha | |
| 5.45 | ppm | signal | 1H | Hg | |
| 6.65 | ppm | doublet | 1H | H6 | $J_{6-5} = 8.70$ Hz |
| 6.90 | ppm | doublet | 3H | H5 | $J_{5-6} = 8.70$ Hz |

Elemental analysis:

| | % C | % H | % N |
|---|---|---|---|
| Calculated: | 74.70 | 9.40 | 4.84 |
| Found: | 74.76 | 9.68 | 4.97 |

PHARMACOLOGICAL STUDY

EXAMPLE A: STUDY OF THE ACUTE TOXICITY

The acute toxicity was assessed after oral administration to batches of 8 mice (26 ### 2 grams). The animals were observed at regular intervals during the first day and daily during the two weeks following the treatment. The LD$_{50}$, resulting in the death of 50% of the animals, was evaluated.

The LD$_{50}$ of the products tested is greater than 1000 mg.kg$^{-1}$, which indicates the low toxicity of the compounds of the invention.

EXAMPLE B: STUDY OF THE BINDING TO MELATONIN RECEPTORS

B1) STUDY ON SHEEP PARS TUBERALIS CELLS

Studies of the binding of the compounds of the invention to melatonin receptors were carried out according to conventional techniques on sheep pars tuberails cells. The pars tuberalis of the adenohypophysis is in fact characterized, in mammals, by a high density of melatonin receptors (Journal of Neuroendocdnology, vol. (1), pp 1–4 (1989)).

PROTOCOL

1) Sheep pars tuberalis membranes are prepared and used as target tissue in saturation experiments in order to determine the binding capacities and affinities for 2-[$^{125}$I] iodomelatonin.

2) Sheep pars tuberalis membranes are used as target tissue, with the various compounds to be tested, in competitive binding experiments with respect to 2-iodomelatonin.

Each experiment is carried out in triplicate and a range of different concentrations is tested for each compound.

The results make it possible to determine, after statistical treatment, the binding affinities of the compound tested.

RESULTS

It appears that the compounds of the invention have a powerful affinity for melatonin receptors since they become attached with a dissociation constant of the order of $10^{-11}$M.

B2) STUDY ON CHICKEN BRAIN CELL MEMBRANES (*GALLUS DOMESTICUS*)

The animals used are 12-day old chickens (*Gallus domesticus*). They are sacrificed between 1300 and 1700 hours on the day of their arrival. The brains are quickly removed and frozen at −200° C. and then stored at −80° C. The membranes are prepared according to the method described by Yuan and Pang (Journal of Endocrinology, 128, pages 475–482, 1991). 2-[$^{125}$I]iodomelatonin is incubated in the presence of the membranes in a buffered solution at pH 7.4 for 60 min at 25° C. At the end of this period, the membrane suspension is filtered (Whatman GF/C). The radioactivity retained on the filter is determined using a Beckman### LS 6000 liquid scintillation counter.

The products used are:
2-[$^{125}$I]iodomelatonin
melatonin
current products
novel molecules In primary screening, the molecules are tested at 2 concentrations ($10^{-7}$ and $10^{-5}$M). Each result is the mean of 3 independent measurements. The active molecules retained after the results of the primary screening were made the subject of a quantitative determination of their efficiency (IC$_{50}$). They are used at 10 different concentrations.

The compounds of the invention have a very strong affinity for melatonin receptors.

EXAMPLE C: FOUR PLATES TEST

The products of the invention are administered via the esophagus to batches of ten mice. One batch receives acacia syrup. 30 minutes after administration of the test products, the animals are placed in compartments, the floor of which comprises four metal plates. Every time the animal passes from one plate to another, it receives a mild electric shock (0.35 mA). The number of transfers from one plate to another is recorded during one minute. After administration, the compounds of the invention significantly increase the number of transfers from one plate to another, demonstrating the anxiolytic activity of the compounds of the invention.

EXAMPLE D: COMPOUNDS OF THE INVENTION ON THE CIRCADIAN RHYTHMS OF RAT LOCOMOTORY ACTIVITY

The involvement of melatonin in controlling, by day/night alternation, the majority of the physiological, biochemical and behavioral circadian rhythms has made it possible to establish a pharmacological model for researching melatoninergic ligands.

The effects of the molecules are tested on many parameters and in particular on the circadian rhythms of locomotory activity which represent a reliable marker for the activity of the endogenous circadian clock.

In this study, the effects of such molecules on a specific experimental model, namely the rat placed in temporal isolation (permanent darkness), are evaluated.

PROTOCOL

Male Long Evans rats, aged one month, are subjected, from their arrival in the laboratory, to a light cycle of 12 h of light per 24 h (LD 12:12).

After adapting for 2 to 3 weeks, they are placed in cages equipped with a wheel connected to a recording system in order to detect the phases of locomotory activity and thus to monitor the nyctohemeral (LD) or circadian (DD) rhythms.

As soon as the rhythms recorded testify to stable control by the light cycle LD 12:12, the rats are placed in permanent darkness (DD).

Two to three weeks later, when the free mode (rhythm reflecting that of the endogenous clock) is clearly established, the rats receive a daily administration of the test molecule.

The observations are carried out by making visible the rhythms of activity:

control of the rhythms of activity by the light rhythm, disappearance of rhythm control in permanent darkness, control by the daily administration of the molecule; transitory or lasting effect.

A computer program makes it possible:

to measure the duration and the intensity of the activity, and the period of the rhythm in animals in free mode and during the treatment, optionally to demonstrate, by spectral analysis, the existence of circadian and noncircadian (ultradian, for example) components.

RESULTS

It clearly appears that the compounds of the invention make it possible to have a powerful effect on the circadian rhythm via the melatoninergic system.

EXAMPLE E: ANTIARRHYTHMIC ACTIVITY

PROTOCOL (Ref: Lawson J. W. et al., J. Pharmacol. Expert. Therap., 160, 22–31, 1968)

The substance tested is administered intraperitoneally to a group of 3 mice 30 min before exposure to anesthesia by chloroform. The animals are then observed for 15 min. The absence of any recording of arrhythmias and of heart rates above 200 beats/min (control: 400–480 beats/min) in two animals at least indicates significant protection.

EXAMPLE F: PLATELET AGGREGATION-INHIBITORY ACTIVITY

PROTOCOL (Ref: Bertele V. et al., Science, 220, 517–519, 1983 ibid, Eur. J. Pharmacol., 85, 331–333, 1982)

The compounds of the invention (100 ###g/ml) are tested for their ability to inhibit the irreversible platelet aggregation induced by sodium arachidonate (50 ###g/ml) in platelet-enriched rabbit plasma.

Inhibition of the maximum aggregation by more than 50% indicates significant activity for the compounds of the invention.

This in vitro test shows that the compounds of the invention are good candidates for the treatment of cardiovascular diseases, in particular thromboses.

EXAMPLE G: EXTENSION OF THE BLEEDING TIME

PROTOCOL (Ref.: Djana E. et al., Thrombosis Research, 15, 191–197, 1979) Butler K. D. et al., Thromb. Haemostasis, 47, 46–49, 1982)

The test compounds are administered orally (100 mg/kg) to a group of 5 mice 1 h before standardized sectioning of the end of each tail (0.5 mm).

The mice are immediately suspended vertically, their tails being immersed for a length of 2 cm in a test tube containing an isotonic saline solution at 37° C.

The time required for the bleeding to stop for a period of 15 seconds is then determined.

An extension in the bleeding time of more than 50% relative to a group of control animals is regarded as significant for the compounds of the invention.

This in vivo test confirms the benefit of the compounds of the invention in the treatment of cardiovascular pathologies since the compounds of the invention extend the bleeding time.

EXAMPLE H: HYPOBARIC HYPOXIA TEST

PROTOCOL (Ref. Gotti B. and Depoortere H., Circ. Cerebrale, Congrès de Circulation Cérébrale [Cerebral Circulation Congress], Toulouse, 105–107, 1979)

The test compounds are administered intraperitoneally (100 mg/kg) to a group of 3 mice 30 minutes before being placed in a chamber at a hypobaric pressure of 20 cm Hg.

The extension in the survival time, with respect to a group of animals treated with the vehicle, of more than 100% and in the absence of a depressant effect on the central nervous system indicates a cerebral protective activity of the compounds of the invention.

EXAMPLE 1: PHARMACEUTICAL COMPOSITION: TABLETS 1000 tablets, containing a dose of 5 mg of N-[2-(7-methoxy-8-allylnaphth-1-yl)-ethyl]acetamide

| | |
|---|---|
| N-[2-(7-Methoxy-8-allylnaphth-1-yl)ethyl]acetamide | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

We claim:
1. A compound selected from those of formula (I):

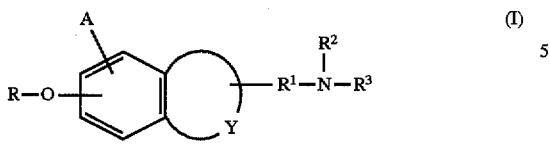

in which:
R$^1$ represents a (C$_1$–C$_4$)alkylene chain which is unsubstituted or substituted by a radical chosen from alkyl, hydroxyl, alkoxycarbonyl, and carboxyl;
R$^2$ represents hydrogen or alkyl;
R$^3$ represents: either a group of formula R$^{31}$

in which n represents zero or an 1 to 3, inclusive, X represents sulfur or oxygen, and R$^5$ represents hydrogen, unsubstituted or substituted alkyl, alkenyl, alkynyl, unsubstituted or substituted cycloalkyl, or an unsubstituted or substituted dicycloalkylalkyl,
or a group of formula R$^{32}$:

in which X' represents oxygen or sulfur, m represents zero or an 1 to 3, inclusive, and R$^6$ represents hydrogen, unsubstituted or substituted alkyl, alkenyl, or alkynyl, it being understood that R$^6$ may also represent unsubstituted or substituted cycloalkyl or unsubstituted or substituted dicycloalkylalkyl when X' is oxygen;
A represents a radical chosen from alkyl of at least two carbon atoms and an A' group chosen from substituted alkyl, alkenyl, and alkynyl,
R represents a group chosen from unsubstituted or substituted alkyl, alkenyl, alkynyl, unsubstituted or substituted cycloalkyl, unsubstituted or substituted cycloalkylalkyl, unsubstituted or substituted aryl, unsubstituted or substituted arylalkyl, unsubstituted or substituted diarylalkyl, cycloalkenyl, and cycloalkenylalkyl,
Y forms, with the benzo ring to which it is bonded, a y$^1$ group which
either represents a group chosen from naphthalene, benzofuran, benzothiophene, and indole, in the case where A represents an A' group,
or represents naphthalene, in the case where A represents alkyl, Y$^1$ optionally being partially hydrogenated,
it being understood that, unless otherwise indicated:
the expression "substituted" relating to the term "alkyl" means that this group is substituted by a radical chosen from halogen, hydroxyl, and alkoxy, the expression "substituted" relating to the terms "cycloalkyl", "cycloalkylalkyl," and "dicycloalkylalkyl" means that these groups are substituted on the cycloalkyl part by a substituent chosen from halogen, alkyl, alkoxy, hydroxyl, and oxo,
the expression "substituted" relating to the terms "aryl", "arylalkyl", and "diarylalkyl" means that these groups are substituted on the aromatic ring by a radical chosen from halogen, alkyl, alkyl substituted by halogen, alkoxy, and hydroxyl,
the terms "alkyl" and "alkoxy" denote linear or branched radicals containing 1 to 6 carbon atoms, inclusive,
the terms "alkenyl" and "alkynyl" denote unsaturated linear or branched radicals containing 2 to 6 carbon atoms, inclusive,
the term "cycloalkyl" denotes a saturated cyclic group containing 3 to 8 carbon atoms, inclusive,
the term "cycloalkenyl" denotes an unsaturated cyclic group containing 3 to 8 carbon atoms, inclusive,
the term "aryl" denotes a phenyl or naphthyl group,
its enantiomers and diastereoisomers, and addition salt thereof with a pharmaceutically-acceptable base.

2. A compound of claim 1, which is N-[2-(7-methoxy-8-allylnaphth-1-yl)ethyl]acetamide.

3. A compound of claim 1, which is N-[2-(7-methoxy-8-propyl-1,2,3,4-tetrahydronaphth-1-yl)ethyl]acetamide or an enantiomer thereof.

4. A compound of claim 1, which is N-[2-(7-methoxy-8-propylnaphth-1-yl) ethyl]acetamide.

5. A compound of claim 1, which is N-[2-(7-methoxy-8-allylnaphth-1-yl) ethyl]butyramide.

6. A compound of claim 1, which is N-[2-(7-methoxy-8-allylnaphth-1-yl) ethyl]cyclopropanecarboxamide.

7. A compound of claim 1, which is N-[2-(7-methoxy-8-allylnaphth-1-yl)ethyl]cyclobutanecarboxamide.

8. A pharmaceutical composition containing a compound of claim 1, in combination with one or a number of pharmaceutically-acceptable excipients.

9. A method of treating a mammal afflicted with a disorder of the melatoninergic system comprising the step of administering to the said mammal an amount of a compound of claim 1 which is effective for alleviating the said disorder.

10. A method of treating a mammal afflicted with a sleep disorder comprising the step of administering to the said mammal an amount of a compound of claim 1 which is effective for alleviating the said disorder.

* * * * *

UNITED STATES PATENT AND TRADEMARK OFFICE
CERTIFICATE OF CORRECTION

PATENT NO. : 5,668,180
DATED : September 16, 1997
INVENTOR(S) : D. Lesieur, P. Depreux, V. Leclerc, P. Delagrange, P. Renard Page 1 of 2

It is certified that error appears in the above-indentified patent and that said Letters Patent is hereby corrected as shown below:

Column 10, line 62: "HYDP-OXYNAPHTH-" should read -- HYDROXYNAPHTH- --.

Column 12, line 1: "AcetonerFoluene" should read -- Acetone/Toluene --

Column 15, line 59: "M ETHOXY-" should read -- METHOXY- --.

Column 18, line 20: "Neuroendocdnology" should read -- Neuroendocrinology".

Column 21, line 19: Delete the word "an" in the sentence.

Column 21, line 22: Delete the word "an" at the end of the line.

UNITED STATES PATENT AND TRADEMARK OFFICE
CERTIFICATE OF CORRECTION

PATENT NO. : 5,668,180
DATED : September 16, 1997
INVENTOR(S) : D. Lesieur, P. Depreux, V. Leclerc, P. Delagrange, P. Renard It is certified that error appears in the above-indentified patent and that said Letters Patent is hereby corrected as shown below:

Column 21, line 30: Delete the word "an" between "or" and "1" at the beginning of the line.

Signed and Sealed this

Tenth Day of February, 1998

Attest:

BRUCE LEHMAN

Attesting Officer

Commissioner of Patents and Trademarks